United States Patent
Wahler

(10) Patent No.: US 10,485,744 B2
(45) Date of Patent: Nov. 26, 2019

(54) DYEING PROCESS STARTING FROM ORTHO-DIPHENOL

(71) Applicant: L'OREAL, Paris (FR)

(72) Inventor: Arno Wahler, Maisons Laffite (FR)

(73) Assignee: L'OREAL, Paris (FR)

( * ) Notice: Subject to any disclaimer, the term of this patent is extended or adjusted under 35 U.S.C. 154(b) by 243 days.

(21) Appl. No.: 15/536,970

(22) PCT Filed: Dec. 18, 2015

(86) PCT No.: PCT/EP2015/080401
§ 371 (c)(1),
(2) Date: Jun. 16, 2017

(87) PCT Pub. No.: WO2016/097246
PCT Pub. Date: Jun. 23, 2016

(65) Prior Publication Data
US 2017/0326048 A1 Nov. 16, 2017

(30) Foreign Application Priority Data

Dec. 19, 2014 (FR) ..................... 14 62864

(51) Int. Cl.
| | | |
|---|---|---|
| *A61Q 5/10* | (2006.01) | |
| *A61K 8/34* | (2006.01) | |
| *A61K 8/27* | (2006.01) | |
| *A61K 8/60* | (2006.01) | |
| *A61K 8/73* | (2006.01) | |
| *A61K 8/97* | (2017.01) | |
| *A61K 8/19* | (2006.01) | |
| *A61K 8/9789* | (2017.01) | |
| *A61K 8/22* | (2006.01) | |
| *A61K 8/36* | (2006.01) | |
| *A61K 8/41* | (2006.01) | |
| *A61K 8/9706* | (2017.01) | |

(52) U.S. Cl.
CPC ................ *A61K 8/347* (2013.01); *A61K 8/19* (2013.01); *A61K 8/22* (2013.01); *A61K 8/27* (2013.01); *A61K 8/36* (2013.01); *A61K 8/41* (2013.01); *A61K 8/604* (2013.01); *A61K 8/608* (2013.01); *A61K 8/73* (2013.01); *A61K 8/731* (2013.01); *A61K 8/737* (2013.01); *A61K 8/97* (2013.01); *A61K 8/9706* (2017.08); *A61K 8/9789* (2017.08); *A61Q 5/10* (2013.01); *A61K 2800/43* (2013.01); *A61K 2800/4324* (2013.01); *A61K 2800/48* (2013.01); *A61K 2800/58* (2013.01); *A61K 2800/88* (2013.01); *A61K 2800/882* (2013.01)

(58) Field of Classification Search
CPC . A61Q 5/10; A61K 8/731; A61K 8/97; A61K 8/498; A61K 8/345; A61K 8/73; A61K 2800/48; A61K 2800/88; A61K 2800/58; A61K 2800/88; A61K 2800/884; A61K 8/604; A61K 8/92; A61K 8/602
See application file for complete search history.

(56) References Cited

U.S. PATENT DOCUMENTS

| | | |
|---|---|---|
| 3,376,110 A | 4/1968 | Shiraeff |
| 3,589,978 A | 6/1971 | Kamal et al. |
| 4,017,460 A | 4/1977 | Tessler |
| 4,031,307 A | 6/1977 | DeMartino et al. |
| 5,008,093 A | 4/1991 | Merianos |
| 5,183,901 A | 2/1993 | Login et al. |
| 5,455,340 A | 10/1995 | Bernard et al. |
| 2002/0124330 A1* | 9/2002 | Pruche ..................... A61K 8/19 8/406 |
| 2003/0103917 A1 | 6/2003 | Pruche |
| 2003/0163878 A1 | 9/2003 | Pruche |
| 2010/0154144 A1* | 6/2010 | Guerin ..................... A61K 8/19 8/424 |
| 2010/0313362 A1 | 12/2010 | Vainshelboim et al. |
| 2014/0150185 A1 | 6/2014 | Lalleman |

FOREIGN PATENT DOCUMENTS

| | | | |
|---|---|---|---|
| FR | 2814943 A1 | 4/2002 | |
| FR | 2814945 A1 | 4/2002 | |
| FR | 2814946 A1 | 4/2002 | |
| FR | 2814947 A1 | 4/2002 | |
| FR | 2968933 * | 6/2012 | ............... A61Q 5/10 |
| FR | 2978039 A1 | 1/2013 | |
| WO | 2010/135237 A1 | 11/2010 | |
| WO | 2011/157666 A1 | 12/2011 | |
| WO | 2012/127502 A1 | 9/2012 | |

OTHER PUBLICATIONS

International Search Report for PCT/EP2015/080401, dated Feb. 10, 2016.
Duram, K., "Effects of pH, temperature and Mordanting Type in Wool Dyeing with the Bark of Cluster Pine (*Pinus brutia* Ten) on Color and Fastness," Chemical Abstracts, Chemical Abstracts Service, XP000663446, Aug. 21, 1995.
Mintel: "Permanent Hair Coloring Kit," Advanced Cosmetic Technologies, XP002666223, Jun. 1, 2009.
Mintel, "Riche-Complete Rejuvenating Care for Dry Skins," Payot AOX, XP002745539, Dec. 1, 2013.
Mintel: "Women's Tonic Shampoo for Thinning Hair," Apivita, XP002745538, Nov. 1, 2011.

* cited by examiner (Continued)

*Primary Examiner* — Eisa B Elhilo
(74) *Attorney, Agent, or Firm* — The Marbury Law Group, PLLC

(57) ABSTRACT

A subject-matter of the invention is a process for dyeing keratinous substances, in particular keratinous fibers, comprising the application, to the said keratinous fibers: of at least one composition A comprising at least one non-ionic alkylpolyglucoside surfactant, at least one metal salt and at least one thickening polymer and of at least one composition B comprising one or more ortho-diphenol derivative(s).

20 Claims, No Drawings

DYEING PROCESS STARTING FROM ORTHO-DIPHENOL

CROSS REFERENCE TO RELATED APPLICATION

This is a national stage application of PCT/EP2015/080401, filed internationally on Dec. 18, 2015, which claims priority to French Application No. 1462864, filed on Dec. 19, 2014, both of which are hereby incorporated by reference in their entireties.

A subject-matter of the invention is a process for dyeing keratinous substances comprising the application of a composition A, comprising at least one non-ionic alkylpolyglucoside surfactant, at least one metal salt and at least one thickening polymer having a sugar unit, and of a composition B comprising one or more ortho-diphenol derivative(s).

It is known to obtain "permanent" colourations with dyeing compositions comprising oxidation dye precursors, generally known as oxidation bases, such as ortho- or para-phenylenediamines, ortho- or para-aminophenols and heterocyclic compounds. These oxidation bases are colourless or weakly coloured compounds, which, when combined with oxidizing products, can give rise to coloured compounds by a process of oxidative condensation. It is also known that the shades obtained can be varied by combining these oxidation bases with couplers or colouring modifiers, the latter being chosen in particular from aromatic meta-diamines, meta-aminophenols, meta-diphenols and certain heterocyclic compounds, such as indole compounds. This oxidation dyeing process consists in applying, to the keratinous fibres, bases or a mixture of bases and couplers with hydrogen peroxide ($H_2O_2$ or aqueous hydrogen peroxide solution) as oxidizing agent, in leaving to diffuse and in then rinsing the fibres. The colourings which result therefrom are permanent, powerful and resistant to external agents, in particular to light, bad weather, washing operations, perspiration and rubbing actions.

However, the commercial hair dyes which contain them can exhibit disadvantages, such as staining and problems of odour, comfort and degradation of the keratinous fibres. This is particularly the case with oxidation dyeing operations.

In the field of dyeing, it is also known to dye keratinous substances, such as the hair or the skin, starting from ortho-diphenol compounds in the presence of a metal salt, in particular a Mn and/or Zn salt. In particular, Patent Applications FR 2 814 943, FR 2 814 945, FR 2 814 946 and FR 2 814 947 provide compositions for dyeing the skin or keratinous fibres comprising a dye precursor which contains at least one ortho-diphenol, Mn and/or Zn oxides and salts, alkaline agents of hydrogencarbonate type in a specific Mn, Zn/hydrogencarbonate ratio and optionally an enzyme. According to these documents, it is possible to obtain intense colourings while dispensing with hydrogen peroxide. However, the colourings obtained are not intense enough, in particular in the case of hair fibres.

There exists a need to develop dyeing processes which make it possible to obtain, on keratinous substances, powerful colourings starting from ortho-diphenols, in particular from a natural extract rich in ortho-diphenols, while limiting the fading thereof. In particular, there exists a need to obtain colourations which are less aggressive for keratinous substances, in particular the hair, and which are simultaneously resistant to external agents (light, bad weather and shampooing operations), which are lasting and uniform, while remaining powerful and chromatic.

The Applicant Company has discovered that it is possible to improve the effectiveness of the colourations starting from ortho-diphenols by employing a process comprising a stage of treatment with a composition in the foaming form comprising a metal salt.

This aim is achieved by the present invention, a subject-matter of which is a process for dyeing keratinous substances, in particular keratinous fibres, comprising:
a) applying to the keratinous substances a composition A comprising at least i) one non-ionic alkylpolyglucoside surfactant, at least ii) one metal salt and at least iii) one thickening polymer and
b) optionally wiping mechanically and/or drying and/or rinsing the said keratinous substances,
c) applying a composition B comprising one or more iv) ortho-diphenol derivative(s), optionally in the presence of hydrogen peroxide or of one or more system(s) which generate(s) hydrogen peroxide and of one or more (bi)carbonate(s).

The process according to the invention exhibits the advantage of dyeing human keratinous substances, in particular keratinous fibres, with powerful and chromatic dyeing results which are resistant to washing operations, perspiration, sebum and light and which are moreover long-lasting, without detrimentally affecting the said keratinous substances. Furthermore, the colourations obtained from the process give uniform colours from the root to the tip of a fibre (low colouration selectivity).

The process according to the invention can be a make-up, dyeing or care process for keratinous substances, in particular the skin, mucous membranes, scalp, lips, nails or keratinous fibres, such as the eyelashes, eyebrows, head hair or body hair. According to one embodiment, the process according to the invention is a process for dyeing keratinous fibres, in particular the hair.

i) Non-ionic Alkylpolyglucoside Surfactants

The non-ionic alkylpolyglucoside surfactants present in the composition A employed in the process according to the invention are surfactants well known from the state of the art. These surfactants can more particularly be represented by the following general formula:

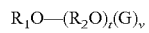

in which $R_1$ represents a linear or branched alkyl and/or alkenyl radical comprising approximately from 8 to 24 carbon atoms, an alkylphenyl radical, the linear or branched alkyl radical of which comprises from 8 to 24 carbon atoms, $R_2$ represents an alkylene radical comprising approximately from 2 to 4 carbon atoms, G represents a sugar unit comprising from 5 to 6 carbon atoms, t denotes a value ranging from 0 to 10, preferably from 0 to 4, and v denotes a value ranging from 1 to 15.

According to a specific embodiment, the alkylpolyglucoside surfactants are compounds with the formula described above in which $R_1$ more particularly denotes a saturated or unsaturated and linear or branched alkyl radical comprising from 8 to 18 carbon atoms, t denotes a value ranging from 0 to 3 and more particularly still equal to 0, and G can denote glucose, fructose or galactose, preferably glucose. The degree of polymerization, i.e. the value of v in the above formula, can range from 1 to 15, preferably from 1 to 4. The mean degree of polymerization is more particularly between 1 and 2.

The glucoside bonds between the sugar units are of 1-6 or 1-4 type and preferably of 1-4 type.

Compounds corresponding to the above formula are in particular represented by the products sold by Cognis under the Plantaren® (600 CS/U, 1200 and 2000) or Plantacare® (818, 1200 and 2000) names. Use may also be made of the products sold by Seppic under the names Triton CG110 (or Oramix CG 10) and Triton CG312 (or Oramix® NS 10), the products sold by BASF under the name Lutensol GD 70 or those sold by Chem Y under the name AG10 LK.

Mention may also be made of the $C_8/C_{16}$ alkyl 1,4-polyglucoside as a 53% aqueous solution sold by Cognis under the reference Plantacare® 818 UP.

According to a specific embodiment of the invention, the content of non-ionic alkylpolyglucoside surfactant(s) varies from 0.1% to 30% by weight, preferably from 1% to 20% by weight and more preferably from 1% to 10% by weight, with respect to the total weight of the composition A.

The composition A can comprise, besides the non-ionic alkylpolyglucoside surfactant(s), additional surfactants which can be chosen from anionic surfactants, non-ionic surfactants different from alkylpolyglucosides, cationic surfactants, amphoteric surfactants, zwitterionic surfactants or their mixtures.

According to one embodiment, the composition A comprises less than 1%, in particular less than 0.5%, of anionic surfactants.

ii) Metal Salt(s)

The process of the invention uses one or more ingredient(s) ii) which are metal salt(s).

In particular, the metal salts are chosen from manganese (Mn) and zinc (Zn) salts.

Within the meaning of the present invention, salts is understood to mean the oxides of these metals and the salts proper resulting in particular from the action of an acid on a metal. Preferably, the salts are not oxides. Mention may be made, among the salts, of halides, such as chlorides, fluorides and iodides, sulfates, phosphates, nitrates, perchlorates and carboxylic acid salts and the polymer complexes which can support the said salts, and also their mixtures.

More particularly, the manganese salt is other than manganese carbonate, manganese hydrogencarbonate or manganese dihydrogencarbonate.

The carboxylic acid salts which can be used in the invention also include salts of hydroxylated carboxylic acids, such as gluconate.

Mention may be made, as example of polymeric complexes which can support the said salts, of manganese pyrrolidonecarboxylate.

Mention may be made, by way of examples, of manganese chloride, manganese fluoride, manganese acetate tetrahydrate, manganese lactate trihydrate, manganese phosphate, manganese iodide, manganese nitrate trihydrate, manganese bromide, manganese perchlorate tetrahydrate, manganese sulfate monohydrate and manganese gluconate. The salts advantageously used are manganese gluconate and manganese chloride.

Mention may be made, among the zinc salts, of zinc sulfate, zinc gluconate, zinc chloride, zinc lactate, zinc acetate, zinc glycinate and zinc aspartate.

The manganese and zinc salts can be introduced in the solid form into the compositions or can originate from a natural, mineral or thermal water which is rich in these ions or also from seawater (Dead Sea water in particular). They can also originate from mineral compounds, such as earths, ochres, such as clays (for example green clay), or even from a plant extract containing them (cf., for example the document FR 2 814 943).

In particular, the metal salts of the invention are in oxidation state II, such as Mn(II) and Zn(II).

According to a preferred embodiment of the invention, the metal salt(s) used represent from 0.001% to 10% by weight approximately of the total weight of the composition A and more preferably still from 0.01% to 0.1% by weight approximately.

iii) Thickening Polymers

The composition A used in the process according to the invention also comprises at least one thickening polymer or a mixture of such polymers.

Within the meaning of the present invention, "thickening polymer" is understood to mean a polymer which, by its presence, makes it possible to increase the viscosity of the composition into which it is introduced. Preferably, a thickening polymer is a polymer which, introduced at 1% by weight into an aqueous solution or an aqueous/alcoholic solution containing 30% ethanol, and at pH 7, makes it possible to confer, on the solution, a viscosity of at least 100 cPs and preferably of at least 500 cPs, at 25° C. and at a shear rate of 1 $s^{-1}$. This viscosity can be measured using a cone/plate viscometer (Haake R600 rheometer or the like).

Advantageously, the thickening polymer(s) are chosen from thickening polymers having a sugar unit or sugar units, comprising one or more sugar units.

"Sugar unit" is understood to mean a unit resulting from a carbohydrate of formula $C_n(H_2O)_{n-1}$ or $(CH_2O)_n$, which can be optionally modified by substitution and/or by oxidation and/or by dehydration.

The sugar units capable of participating in the composition of the polymers of the invention preferably result from the following sugars: glucose, galactose, arabinose, rhamnose, mannose, xylose, fucose, fructose, anhydrogalactose, galacturonic acid, glucuronic acid, mannuronic acid, galactose sulfate or anhydrogalactose sulfate.

The polymers having a sugar unit or sugar units according to the invention can be of natural or synthetic origin. They can be non-ionic, anionic, amphoteric or cationic. The base units of the polymers having a sugar unit of the invention can be mono- or disaccharides.

Mention may in particular be made, as polymers capable of being employed, of the following native gums, and also their derivatives:

a) tree or shrub exudates, including:
gum arabic (branched polymer of galactose, arabinose, rhamnose and glucuronic acid),
ghatti gum (polymer resulting from arabinose, galactose, mannose, xylose and glucuronic acid),
karaya gum (polymer resulting from galacturonic acid, galactose, rhamnose and glucuronic acid),
gum tragacanth (polymer of galacturonic acid, galactose, fucose, xylose and arabinose), b) gums resulting from algae, including:
agar (polymer resulting from galactose and anhydrogalactose),
alginates (polymers of mannuronic acid and glucuronic acid),
carrageenans and furcellerans (polymers of galactose sulfate and anhydrogalactose sulfate), c) gums resulting from seeds or tubers, including:
guar gum (polymer of mannose and galactose),
locust bean gum (polymer of mannose and galactose),
fenugreek gum (polymer of mannose and galactose),
tamarind gum (polymer of galactose, xylose and glucose),
konjac gum (polymer of glucose and mannose), d) microbial gums, including:
xanthan gum (polymer of glucose, mannose acetate, mannose/pyruvic acid and glucuronic acid), gellan gum (polymer of partially acylated glucose, of rhamnose and of glucuronic acid),
scleroglucan gum (glucose polymer),
e) plant extracts, including:
cellulose (glucose polymer),
starch (glucose polymer),
inulin (polymer of fructose and glucose).

These polymers can be physically or chemically modified. Mention may in particular be made, as physical treatment, of the temperature. Mention may be made, as chemical treatments, of esterification, etherification, amidation or oxidation reactions. These treatments make it possible to result in polymers which can be non-ionic, anionic, cationic or amphoteric.

Preferably, these chemical or physical treatments are applied to guar gums, locust bean gums, starches and celluloses.

The non-ionic guar gums which can be used according to the invention can be modified with $C_1$-$C_6$ hydroxyalkyl groups. Mention may be made, among the hydroxyalkyl groups, of the hydroxymethyl, hydroxyethyl, hydroxypropyl and hydroxybutyl groups.

These guar gums are well known from the state of the art and can, for example, be prepared by reacting corresponding alkene oxides, such as, for example, propylene oxides, with the guar gum, so as to obtain a guar gum modified with hydroxypropyl groups.

The degree of hydroxyalkylation preferably varies from 0.4 to 1.2 and corresponds to the number of alkylene oxide molecules consumed by the number of free hydroxyl functional groups present on the guar gum.

Such non-ionic guar gums optionally modified with hydroxyalkyl groups are sold, for example, under the trade names Jaguar HP8, Jaguar HP60 and Jaguar HP120 by Rhodia Chimie.

The guar gums modified with cationic groups which can more particularly be used according to the invention are guar gums comprising trialkylammonium cationic groups. Preferably, from 2% to 30% by number of the hydroxyl functional groups of these guar gums carry trialkylammonium cationic groups. More preferably still, from 5% to 20% by number of the hydroxyl functional groups of these guar gums are branched with trialkylammonium cationic groups. Mention may very particularly be made, among these trialkylammonium groups, of the trimethylammonium and triethylammonium groups. More preferably still, these groups represent from 5% to 20% by weight, with respect to the total weight of the modified guar gum.

According to the invention, use may be made of guar gums modified with 2,3-epoxypropyltrimethylammonium chloride.

These guar gums modified with cationic groups are products already known per se and are, for example, described in U.S. Pat. No. 3,589,578 and U.S. Pat. No. 4,031,307. Such products are moreover sold in particular under the trade names Jaguar C13 S, Jaguar C 15 and Jaguar C 17 by Rhodia Chimie.

Use may be made, as modified locust bean gum, of the cationic locust bean gum containing hydroxypropyltrimonium groups, such as Catinal CLB 200 provided by Toho.

The starch molecules used in the present invention can originate from any plant starch source, in particular cereals and tubers; more particularly, they can be starches from maize, rice, cassava, barley, potato, wheat, sorghum, pea, oat or tapioca. Use may also be made of the hydrolysates of the abovementioned starches. The starch preferably results from potato. The starches can be chemically or physically modified, in particular by one or more of the following reactions: pregelatinization, oxidation, crosslinking, esterification, etherification, amidation or heat treatments.

More particularly, these reactions can be carried out in the following way:
pregelatinization by splitting the starch granules (for example drying and cooking in a drying drum);
oxidation with strong oxidizing agents, resulting in the introduction of carboxyl groups into the starch molecule and in the depolymerization of the starch molecule (for example by treating an aqueous starch solution with sodium hypochlorite);
crosslinking with functional agents capable of reacting with the hydroxyl groups of the starch molecules, which will thus be bonded together (for example with glyceryl and/or phosphate groups);
esterification in alkaline medium for the grafting of functional groups, in particular $C_1$-$C_6$ acyl (acetyl), $C_1$-$C_6$ hydroxyalkyl (hydroxyethyl or hydroxypropyl), carboxymethyl or octenylsuccinic.

It is possible in particular to obtain, by crosslinking with phosphorus compounds, monostarch phosphates (of the type St-O—PO—$(OX)_2$), distarch phosphates (of the type St-O—PO—(OX)—O-St) or even tristarch phosphates (of the type St-O—PO—$(O\text{-}St)_2$) or their mixtures, with St meaning starch and X denoting in particular alkali metals (for example sodium or potassium), alkaline earth metals (for example calcium or magnesium), the ammonium ion, amine ions, such as those of monoethanolamine, diethanolamine, triethanolamine or 3-amino-1,2-propanediol, or ammonium ions resulting from basic amino acids, such as lysine, arginine, sarcosine, ornithine or citrulline.

The phosphorus compounds can, for example, be sodium tripolyphosphate, sodium orthophosphate, phosphorus oxychloride or sodium trimetaphosphate.

Use will preferably be made of distarch phosphates or compounds rich in distarch phosphate, such as the product sold under the references Prejel VA-70-T AGGL (gelatinized hydroxypropyl cassava distarch phosphate), Prejel TK1 (gelatinized cassava distarch phosphate) and Prejel 200 (gelatinized acetyl cassava distarch phosphate) by Avebe, or Structure Zea from National Starch (gelatinized corn distarch phosphate).

A preferred starch is a starch which has undergone at least one chemical modification, such as at least one esterification.

According to the invention, use may also be made of amphoteric starches comprising one or more anionic groups and one or more cationic groups. The anionic and cationic groups can be bonded to the same reactive site of the starch molecule or to different reactive sites; they are preferably bonded to the same reactive site. The anionic groups can be of carboxylic, phosphate or sulfate type, preferably of carboxylic type. The cationic groups can be of primary, secondary, tertiary or quaternary amine type.

The amphoteric starches are in particular chosen from the compounds having the following formulae:

$$\text{St}-\text{O}-(\text{CH}_2)_n-\text{N} \begin{matrix} \text{HC}-\overset{R'}{\underset{H}{\overset{|}{C}}}-\text{COOM} \\ \text{H} \phantom{x} \text{H} \\ \overset{|}{C}-\overset{|}{C}-\text{COOM} \\ R' \phantom{x} R \end{matrix} \qquad (I)$$

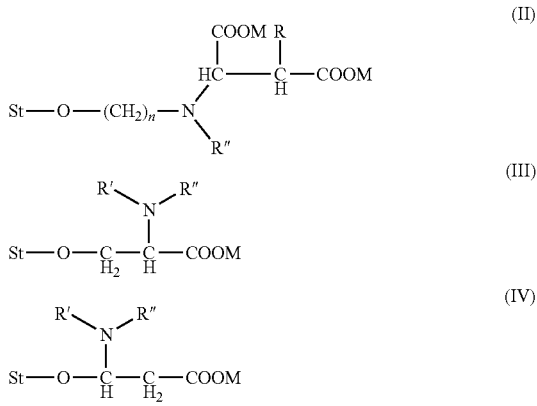

in which:

St-O represents a starch molecule,

R, which are identical or different, represent a hydrogen atom or a methyl radical, R', which are identical or different, represent a hydrogen atom, a methyl radical or a —COOH group, n is an integer equal to 2 or 3, M, which are identical or different, denote a hydrogen atom, an alkali metal or alkaline earth metal, such as Na, K, Li or $NH_4$, a quaternary ammonium or an organic amine, R" represents a hydrogen atom or a $C_1$-$C_{18}$ alkyl radical.

These compounds are in particular described in U.S. Pat. No. 5,455,340 and U.S. Pat. No. 4,017,460.

Use is in particular made of the starches of formulae (II) or (III); and preferably starches modified with 2-chloroethylaminodipropionic acid, that is to say the starches of formula (II) or (III) in which R, R', R" and M represent a hydrogen atom and n is equal to 2. The preferred amphoteric starch is a starch chloroethylamidodipropionate.

The celluloses and cellulose derivatives can be anionic, cationic, amphoteric or non-ionic. Among these derivatives, cellulose ethers, cellulose esters and cellulose ester ethers are distinguished.

Mention may be made, among the cellulose esters, of inorganic cellulose esters (cellulose nitrates, sulfates or phosphates), organic cellulose esters (cellulose monoacetates, triacetates, amidopropionates, acetate butyrates, acetate propionates or acetate trimellitates), and mixed organic/inorganic cellulose esters, such as cellulose acetate butyrate sulfates and cellulose acetate propionate sulfates.

Mention may be made, among the cellulose ester ethers, of hydroxypropyl methylcellulose phthalates and ethylcellulose sulfates.

Mention may be made, among the non-ionic cellulose ethers, of alkylcelluloses, such as methylcelluloses and ethylcelluloses (for example Ethocel Standard 100 Premium from Dow Chemical); hydroxyalkylcelluloses, such as hydroxyethylcelluloses and hydroxyethylcelluloses (for example Natrosol 250 HHR provided by Aqualon) and hydroxypropylcellulose (for example Klucel EF from Aqualon); and mixed hydroxyalkyl alkylcelluloses, such as hydroxypropyl methylcelluloses (for example Methocel E4M from Dow Chemical), hydroxyethyl methylcelluloses, hydroxyethyl ethylcelluloses (for example Bermocoll E 481 FQ from Akzo Nobel) and hydroxybutyl methylcelluloses.

Mention may be made, among the anionic cellulose ethers, of carboxyalkylcelluloses and their salts. Mention may be made, as examples, of carboxymethylcelluloses, carboxymethyl methylcelluloses (for example Blanose 7M from Aqualon) and carboxymethyl hydroxyethylcelluloses, and also their sodium salts.

Mention may be made, among the cationic cellulose ethers, of crosslinked or non-crosslinked quaternized hydroxyethylcelluloses. The quaternizing agent can in particular be diallyldimethylammonium chloride (for example Celquat L200 from National Starch). Mention may be made, as other cationic cellulose ether, of hydroxyethylcellulose hydroxypropyltrimethylammonium chloride (for example Ucare polymer JR 400 from Amerchol).

Mention may be made, among the associative thickening polymers having a sugar unit or sugar units, of celluloses or their derivatives, modified with groups comprising at least one fatty chain, such as alkyl, arylalkyl or alkylaryl groups or their mixtures where the alkyl groups are $C_8$-$C_{22}$ groups; non-ionic alkyl hydroxyethylcelluloses, such as the products Natrosol Plus Grade 330 CS and Polysurf 67 ($C_{16}$ alkyl) sold by Aqualon; quaternized alkyl hydroxyethylcelluloses (cationic), such as the products Quatrisoft LM 200, Quatrisoft LM-X 529-18-A, Quatrisoft LM-X 529-18-B ($C_{12}$ alkyl) and Quatrisoft LM-X 529-8 ($C_{18}$ alkyl) sold by Amerchol, the products Crodacel QM, Crodacel QL ($C_{12}$ alkyl) and Crodacel QS ($C_{18}$ alkyl) sold by Croda, and the product Softcat SL 100 sold by Amerchol; non-ionic nonoxynyl hydroxyethylcelluloses, such as the product Amercell HM-1500 sold by Amerchol; or non-ionic alkylcelluloses, such as the product Bermocoll EHM 100 sold by Berol Nobel.

Mention may be made, as associative polymers having a sugar unit or sugar units derived from guar, of hydroxypropyl guars modified with a fatty chain, such as the product Esaflor HM 22 (modified with a $C_{22}$ alkyl chain) sold by Lamberti, the product Miracare XC 95-3 (modified with a $C_{14}$ alkyl chain) and the product RE 205-146 (modified with a $C_{20}$ alkyl chain) sold by Rhodia Chimie.

The polymer(s) having a sugar unit or sugar units of the invention are preferably chosen from guar gums, locust bean gums, xanthan gums, starches and celluloses, in their modified form (derivatives) or unmodified form.

Preferably, the thickening polymers according to the invention are non-ionic or cationic thickening polymers having a sugar unit or sugar units. Preferably, the thickening polymer is chosen from celluloses and their derivatives, preferably non-ionic celluloses and their derivatives, more preferably from non-ionic cellulose ethers, such as hydroxyalkylcelluloses.

The composition according to the invention comprises the thickening polymer(s) preferably in an amount ranging from 0.01% to 10% by weight, in particular from 0.05% to 5% by weight, preferably from 0.1% to 5% by weight, indeed even from 0.5% to 3% by weight, with respect to the total weight of the composition A.

iv) Ortho-Diphenol Derivative(s):

The process according to the invention employs a composition B comprising an ortho-diphenol derivative iv).

A specific embodiment of the invention relates to ortho-diphenol derivatives or mixtures of compounds comprising at least one aromatic ring, preferably a benzene ring, comprising at least two hydroxyl (OH) groups carried by two adjacent carbon atoms of the aromatic ring. In particular, the ortho-diphenol derivative or derivatives according to the invention are not self-oxidizable derivatives having an indole unit. More particularly, they are different from 5,6-dihydroxyindole.

The aromatic ring can more particularly be a fused aryl or fused heteroaromatic ring, i.e. optionally comprising one or more heteroatoms, such as benzene, naphthalene, tetrahydronaphthalene, indane, indene, anthracene, phenanthrene, isoindole, indoline, isoindoline, benzofuran, dihydrobenzofuran, chroman, isochroman, chromene, isochromene, quinoline, tetrahydroquinoline and isoquinoline, the said aromatic ring comprising at least two hydroxyl groups carried by two adjacent carbon atoms of the aromatic ring. Preferably, the aromatic ring of the ortho-diphenol derivatives according to the invention is a benzene ring.

The term "fused ring" is understood to mean that at least two saturated or unsaturated and heterocyclic or non-heterocyclic rings exhibit a common bond, i.e. that at least one ring is placed side by side with another ring.

The ortho-diphenols according to the invention may or may not be salified. They can also be in the aglycone form (without bonded sugar) or in the form of glycosylated compounds.

More particularly, the ortho-diphenol derivative iv) represents a compound of formula (I), or one of its oligomers, in salified or non-salified form:

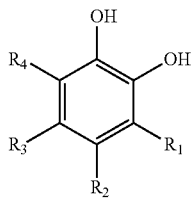

(I)

in which formula (I) the substituents:
$R_1$ to $R_4$, which are identical or different, represent:
  a hydrogen atom,
  a halogen atom,
  a hydroxyl radical,
  a carboxyl radical,
  an alkyl carboxylate or alkoxycarbonyl radical,
  an optionally substituted amino radical,
  an optionally substituted and linear or branched alkyl radical,
  an optionally substituted and linear or branched alkenyl radical,
  an optionally substituted cycloalkyl radical,
  an alkoxy radical,
  an alkoxyalkyl radical,
  an alkoxyaryl radical, it being possible for the aryl group to be optionally substituted,
  an aryl radical,
  a substituted aryl radical,
  a saturated or unsaturated heterocyclic radical carrying or not carrying a cationic or anionic charge, optionally substituted and/or optionally fused with an aromatic ring, preferably a benzene ring, the said aromatic ring being optionally substituted, in particular with one or more hydroxyl or glycosyloxy groups,
  a radical containing one or more silicon atoms,
  where two of the substituents carried by two adjacent carbon atoms $R_1$-$R_2$, $R_2$-$R_3$ or $R_3$-$R_4$ form, together with the carbon atoms carrying them, a saturated or unsaturated and aromatic or non-aromatic ring optionally containing one or more heteroatoms and optionally fused with one or more saturated or unsaturated rings optionally containing one or more heteroatoms. In particular, $R_1$ to $R_4$ together form from one to four rings.

A specific embodiment of the invention relates to ortho-diphenol derivatives of formula (I), two adjacent substituents $R_1$-$R_2$, $R_2$-$R_3$ or $R_3$-$R_4$ of which cannot form, with the carbon atoms which carry them, a pyrrolyl radical. More particularly, $R_2$ and $R_3$ cannot form a pyrrolyl radical fused to the benzene ring carrying the two hydroxyl groups.

The saturated or unsaturated and optionally fused rings can also be optionally substituted.

The alkyl radicals are saturated and linear or branched hydrocarbon radicals, generally $C_1$-$C_{20}$ hydrocarbon radicals, in particular $C_1$-$C_{10}$ hydrocarbon radicals, preferably $C_1$-$C_6$ alkyl radicals, such as methyl, ethyl, propyl, butyl, pentyl and hexyl.

The alkenyl radicals are unsaturated and linear or branched $C_2$-$C_{20}$ hydrocarbon radicals, preferably comprising at least one double bond, such as ethylene, propylene, butylene, pentylene, 2-methylpropylene and decylene.

The aryl radicals are monocyclic or fused or nonfused polycyclic carbon-based radicals, preferably comprising from 6 to 30 carbon atoms, at least one ring of which is aromatic; the choice is preferably made, from the aryl radical, of a phenyl, biphenyl, naphthyl, indenyl, anthracenyl and tetrahydronaphthyl.

The alkoxy radicals are alkyl-oxy radicals with alkyl as defined above, preferably $C_1$-$C_{10}$ alkyl, such as methoxy, ethoxy, propoxy and butoxy.

The alkoxyalkyl radicals are preferably $(C_1$-$C_{20})$alkoxy $(C_1$-$C_{20})$alkyl radicals, such as methoxymethyl, ethoxymethyl, methoxyethyl, ethoxyethyl, and the like.

The cycloalkyl radicals are generally $C_4$-$C_8$ cycloalkyl radicals, preferably the cyclopentyl and cyclohexyl radicals. The cycloalkyl radicals can be substituted cycloalkyl radicals, in particular substituted by alkyl, alkoxy, carboxylic acid, hydroxyl, amine and ketone groups.

The alkyl or alkenyl radicals, when they are optionally substituted, can be substituted by at least one substituent carried by at least one carbon atom, chosen from:
  a halogen atom;
  a hydroxyl group;
  a $C_1$-$C_2$ alkoxy radical;
  a $C_1$-$C_{10}$ alkoxycarbonyl radical;
  a (poly)hydroxy($C_2$-$C_4$)alkoxy radical;
  an amino radical;
  a 5- or 6-membered heterocycloalkyl radical;
  an optionally cationic 5- or 6-membered heteroaryl radical, preferably an imidazolium radical, optionally substituted with a $(C_1$-$C_4)$alkyl radical, preferably a methyl radical;
  an amino radical substituted with one or two identical or different $C_1$-$C_6$ alkyl radicals optionally carrying at least:
    one hydroxyl group;
    an amino group optionally substituted with one or two optionally substituted $C_1$-$C_3$ alkyl radicals, it being possible for the said alkyl radicals to form, with the nitrogen atom to which they are attached, a saturated or unsaturated and optionally substituted 5- to 7-membered heterocycle optionally comprising at least one other heteroatom different or not different from nitrogen;
    a quaternary ammonium group —N⁺R'R"R'" M⁻ for which R', R" and R'", which are identical or different, represent a hydrogen atom or a $C_1$-$C_4$ alkyl group and M⁻ represents the counterion of the corresponding organic or inorganic acid or of the corresponding halide;

or an optionally cationic 5- or 6-membered heteroaryl radical, preferably an imidazolium radical, optionally substituted with a ($C_1$-$C_4$)alkyl radical, preferably a methyl radical;

an acylamino (—NR—COR') radical in which the R radical is a hydrogen atom or a $C_1$-$C_4$ alkyl radical optionally carrying at least one hydroxyl group and the R' radical is a $C_1$-$C_2$ alkyl radical; a carbamoyl (($R)_2$N—CO—) radical in which the R radicals, which are identical or different, represent a hydrogen atom or a $C_1$-$C_4$ alkyl radical optionally carrying at least one hydroxyl group; an alkylsulfonylamino (R'$SO_2$—NR—) radical in which the R radical represents a hydrogen atom or a $C_1$-$C_4$ alkyl radical optionally carrying at least one hydroxyl group and the R' radical represents a $C_1$-$C_4$ alkyl radical or a phenyl radical; or an aminosulfonyl (($R)_2$N—$SO_2$—) radical in which the R radicals, which are identical or different, represent a hydrogen atom or a $C_1$-$C_4$ alkyl radical optionally carrying at least one hydroxyl group;

a carboxyl radical in the acid or salified form (preferably in the form salified with an alkali metal or a substituted or unsubstituted ammonium);

a cyano group;

a nitro group;

a carboxyl or glycosylcarbonyl group;

a phenylcarbonyloxy group optionally substituted with one or more hydroxyl groups;

a glycosyloxy group; and a phenyl group optionally substituted with one or more hydroxyl groups.

The aryl or heterocyclic radicals or the aryl or heterocyclic part of the radicals, when they are optionally substituted, can be substituted with at least one substituent carried by at least one carbon atom chosen from:

a $C_1$-$C_{10}$ and preferably $C_1$-$C_8$ alkyl radical optionally substituted with one or more radicals chosen from the following radicals: hydroxyl, $C_1$-$C_2$ alkoxy, (poly)hydroxy($C_2$-$C_4$)alkoxy, acylamino, amino substituted with two identical or different $C_1$-$C_4$ alkyl radicals optionally carrying at least one hydroxyl group, or it being possible for the two radicals to form, with the nitrogen atom to which they are attached, a saturated or unsaturated and optionally substituted 5- to 7-membered and preferably 5- or 6-membered heterocycle optionally comprising another heteroatom identical to or different from nitrogen;

a halogen atom;

a hydroxyl group;

a $C_1$-$C_2$ alkoxy radical;

a $C_1$-$C_{10}$ alkoxycarbonyl radical;

a (poly)hydroxy($C_2$-$C_4$)alkoxy radical;

an amino radical;

a 5- or 6-membered heterocycloalkyl radical;

an optionally cationic 5- or 6-membered heteroaryl radical, preferably an imidazolium radical, optionally substituted with a ($C_1$-$C_4$)alkyl radical, preferably a methyl radical;

an amino radical substituted with one or two identical or different $C_1$-$C_6$ alkyl radicals optionally carrying at least:
one hydroxyl group;
an amino group optionally substituted with one or two optionally substituted $C_1$-$C_3$ alkyl radicals, it being possible for the said alkyl radicals to form, with the nitrogen atom to which they are attached, a saturated or unsaturated and optionally substituted 5- to 7-membered heterocycle optionally comprising at least one other heteroatom different or not different from nitrogen;

a quaternary ammonium group —$N^+$R'R''R''' $M^-$ for which R', R'' and R''', which are identical or different, represent a hydrogen atom or a $C_1$-$C_4$ alkyl group and $M^-$ represents the counterion of the corresponding organic or inorganic acid or of the corresponding halide;

or an optionally cationic 5- or 6-membered heteroaryl radical, preferably an imidazolium radical, optionally substituted with a ($C_1$-$C_4$)alkyl radical, preferably a methyl radical;

an acylamino (—NR—COR') radical in which the R radical is a hydrogen atom or a $C_1$-$C_4$ alkyl radical optionally carrying at least one hydroxyl group and the R' radical is a $C_1$-$C_2$ alkyl radical; a carbamoyl (($R)_2$N—CO—) radical in which the R radicals, which are identical or different, represent a hydrogen atom or a $C_1$-$C_4$ alkyl radical optionally carrying at least one hydroxyl group; an alkylsulfonylamino (R'$SO_2$—NR—) radical in which the R radical represents a hydrogen atom or a $C_1$-$C_4$ alkyl radical optionally carrying at least one hydroxyl group and the R' radical represents a $C_1$-$C_4$ alkyl radical or a phenyl radical; or an aminosulfonyl (($R)_2$N—$SO_2$—) radical in which the R radicals, which are identical or different, represent a hydrogen atom or a $C_1$-$C_4$ alkyl radical optionally carrying at least one hydroxyl group;

a carboxyl radical in the acid or salified form (preferably in the form salified with an alkali metal or a substituted or unsubstituted ammonium);

a cyano group;

a nitro group;

a polyhaloalkyl group, preferentially the trifluoromethyl group;

a carboxyl or glycosylcarbonyl group;

a phenylcarbonyloxy group optionally substituted with one or more hydroxyl groups;

a glycosyloxy group; and a phenyl group optionally substituted with one or more hydroxyl groups.

The term "glycosyl radical" is understood to mean a radical resulting from a mono- or polysaccharide.

The radicals comprising one or more silicon atoms are preferably polydimethylsiloxane, polydiphenylsiloxane, polydimethylphenylsiloxane or stearoxy dimethicone radicals.

The heterocyclic radicals are generally radicals comprising, in at least one ring, one or more heteroatoms chosen from O, N and S, preferably O or N, optionally substituted by in particular one or more alkyl, alkoxy, carboxylic acid, hydroxyl, amine or ketone groups. These rings can contain one or more oxo groups on the carbon atoms of the heterocycle.

Mention may be made, among the heterocyclic radicals which can be used, of the furyl, pyranyl, pyrrolyl, imidazolyl, pyrazolyl, pyridyl or thienyl groups.

More preferably, the heterocyclic groups are fused groups, such as benzofuranyl, chromenyl, xanthenyl, indolyl, isoindolyl, quinolyl, isoquinolyl, chromanyl, isochromanyl, indolinyl, isoindolinyl, coumarinyl or isocoumarinyl groups, it being possible for these groups to be substituted, in particular by one or more OH groups.

The ortho-diphenols of use in the process of the invention can be natural or synthetic. The natural ortho-diphenols include the compounds which can be present in nature and which are reproduced by chemical (semi)synthesis.

The salts of the ortho-diphenols of the invention can be salts of acids or of bases. The acids can be inorganic or organic. Preferably, the acid is hydrochloric acid, which results in chlorides.

The bases can be inorganic or organic. In particular, the bases are alkali metal hydroxides, such as sodium hydroxide, which results in sodium salts.

According to a specific embodiment of the invention, the composition comprises, as ingredient iv), one or more synthetic ortho-diphenol derivative(s) which do not exist in nature.

According to another preferred embodiment of the invention, the process for dyeing keratinous substances uses, as ingredient iv), one or more natural ortho-diphenol derivative(s).

More particularly, the ortho-diphenols which can be used in the process of the invention according to iv) are in particular:
flavanols, such as catechin and epicatechin gallate,
flavonols, such as quercetin,
anthocyanidins, such as cyanidin, delphinidin or petunidin,
anthocyanins or anthocyans, such as myrtillin,
ortho-hydroxybenzoates, for example gallic acid salts,
flavones, such as luteolin,
hydroxystilbenes, for example 3,3',4,5'-tetrahydroxystilbene, optionally oxylated (for example glucosylated),
3,4-dihydroxyphenylalanine and its derivatives,
2,3-dihydroxyphenylalanine and its derivatives,
4,5-dihydroxyphenylalanine and its derivatives,
dihydroxycinnamates, such as caffeic acid and chlorogenic acid,
ortho-polyhydroxycoumarins,
ortho-polyhydroxyisocoumarins,
ortho-polyhydroxycoumarones,
ortho-polyhydroxyisocoumarones,
ortho-polyhydroxychalcones,
ortho-polyhydroxychromones,
ortho-polyhydroxyquinones,
ortho-polyhydroxyxanthones,
1,2-dihydroxybenzene and its derivatives,
1,2,4-trihydroxybenzene and its derivatives,
1,2,3-trihydroxybenzene and its derivatives,
2,4,5-trihydroxytoluene and its derivatives,
proanthocyanidins and in particular proanthocyanidins A1, A2, B1, B2, B3 and C1,
proanthocyanins,
tannic acid,
ellagic acid,
and the mixtures of the preceding compounds.

When the dyeing precursors exhibit D and L forms, both forms can be used in the compositions according to the invention, as can the racemates.

According to one embodiment, the natural ortho-diphenols result from extracts of animals, bacteria, fungi, algae or plants, used in their entirety or partially. In particular as regards plants, the extracts result from plants or plant parts, such as fruit, including citrus fruit, vegetables, trees or shrubs. Use may also be made of mixtures of these extracts, which are rich in ortho-diphenols as defined above.

Preferably, the natural ortho-diphenol(s) of the invention result from extracts of plants or plant parts.

Within the meaning of the invention, the said extracts will be put, in their entirety, into the same category as compound iv).

The extracts are obtained by extraction of various plant parts, such as, for example, the root, the wood, the bark, the leaf, the flower, the fruit, the seed, the pod or the peel.

Mention may be made, among the plant extracts, of extracts of tea and rose leaves, extracts of rosemary leaves and extracts of mate leaves.

Mention may be made, among the extracts of fruit, of extracts of apple, extracts of grape (in particular of grape seed) or extracts of cocoa beans and/or pods.

Mention may be made, among the extracts of vegetables, of extracts of potato or of onion peel.

Mention may be made, among the extracts of tree wood, of extracts of pine bark or extracts of logwood.

Use may also be made of mixtures of plant extracts.

According to a specific embodiment of the invention, the ortho-diphenol derivative(s) are natural extracts rich in ortho-diphenols. According to a preferred form, the ortho-diphenol derivative(s) are solely natural extracts.

The natural extracts according to the invention can be provided in the form of powders or liquids. Preferably, the extracts of the invention are provided in the form of powders.

According to the invention, the synthetic ortho-diphenol derivative(s), the natural ortho-diphenol derivative(s) and/or the natural extract(s) used as ingredient iv) in one or more composition(s) of use in the process according to the invention preferably represent(s) from 0.001% to 20% by weight of the total weight of the composition(s) containing the ortho-diphenol(s) or the extract(s).

As regards the pure ortho-diphenols, the content in the composition B is preferably between 0.001% and 5% by weight of the composition.

As regards the extracts, the content in the composition B is preferably between 0.5% and 20% by weight of the composition.

v) Hydrogen Peroxide or System(s) which Generate(s) Hydrogen Peroxide,

According to one embodiment, the process according to the invention employs hydrogen peroxide or one or more system(s) which generate(s) hydrogen peroxide which can be present in the composition B or introduced via an additional composition.

The system(s) which generate(s) hydrogen peroxide can be chosen from:
a) urea hydrogen peroxide;
b) polymeric complexes which can release hydrogen peroxide, such as polyvinylpyrrolidone/$H_2O_2$, in particular existing in the form of powders, and the other polymeric complexes described in U.S. Pat. No. 5,008,093, U.S. Pat. No. 3,376,110 and U.S. Pat. No. 5,183,901;
c) oxidases which produce hydrogen peroxide in the presence of an appropriate substrate (for example glucose in the case of glucose oxidase or uric acid with uricase);
d) metal peroxides which generate hydrogen peroxide in water, such as calcium peroxide or magnesium peroxide;
e) perborates; or
f) percarbonates.

According to a preferred embodiment of the invention, le composition B contains hydrogen peroxide.

Moreover, the composition(s) comprising hydrogen peroxide or generator(s) of hydrogen peroxide can also include various adjuvants conventionally used in hair dyeing compositions and as defined hereinbelow.

According to a specific embodiment of the invention, the hydrogen peroxide or the system(s) which generate(s) hydrogen peroxide used preferably represent(s) from 0.001% to 12% by weight, expressed as hydrogen peroxide, with respect to the total weight of the composition(s) containing it (them), and more preferably still from 0.2% to 2.7% by weight.

vi) Basic Compound(s) with a pKa Greater than 7

According to one embodiment, the process according to the invention employs one or more basic compound(s) with a pKa greater than 7 which can be present in the composition B or introduced via an additional composition.

The basic compound(s) with a pKa greater than 7 can be inorganic, organic or hybrid.

The basic inorganic compound(s) with a pKa greater than 7 are, for example, chosen from aqueous ammonia, alkali metal carbonates or bicarbonates, such as sodium carbonate, sodium bicarbonate, potassium carbonate or potassium bicarbonate, sodium hydroxide or potassium hydroxide, or their mixtures.

The basic organic compound(s) with a pKa greater than 7 are, for example, chosen from alkanolamines, in particular monoethanolamine (MEA), oxyethylenated and/or oxypropylenated ethylenediamines, amino acids, in particular basic amino acids, in the neutral or ionic form, and the compounds of following formula (V):

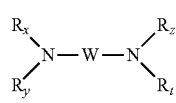

(V)

in which formula (V) W is a divalent $C_1$-$C_6$ alkylene radical optionally substituted with one or more hydroxyl groups or a $C_1$-$C_6$ alkyl radical and/or optionally interrupted with one or more heteroatoms, such as 0, or $NR_u$, and $R_x$, $R_y$, $R_z$, $R_t$ and $R_u$, which are identical or different, represent a hydrogen atom or a $C_1$-$C_6$ alkyl, $C_1$-$C_6$ hydroxyalkyl or $C_1$-$C_6$ aminoalkyl radical.

Preferably, the basic compound(s) with a pKa greater than 7 are chosen from one or more (bi)carbonates.

The term "(bi)carbonates" is understood to mean:

A) carbonates of alkali metals ($Met^+_2 CO_3^{2-}$), of alkaline earth metals ($Met'^{2+}CO_3^{2-}$), of ammonium (($R''_4N^+)_2 CO_3^{2-}$) or of phosphonium (($R''_4P^+)_2 CO_3^{2-}$), with Met' representing an alkaline earth metal, Met representing an alkali metal and R", which are identical or different, representing a hydrogen atom or an optionally substituted ($C_1$-$C_6$)alkyl group, such as a hydroxyethyl group, and B) bicarbonates, also known as hydrogencarbonates, with the following formulae:

$R'^+HCO_3^-$ with R' representing a hydrogen atom, an alkali metal, an ammonium group $R''_4N^+$— or a phosphonium group $R''_4P^+$—, where R", which are identical or different, represent a hydrogen atom or an optionally substituted ($C_1$-$C_6$)alkyl group, such as hydroxyethyl, and, when R' represents a hydrogen atom, the hydrogencarbonate is then known as dihydrogencarbonate ($CO_2 H_2O$); and $Met'^{2+} (HCO_3^-)_2$, with Met' representing an alkaline earth metal.

More particularly, the compound vi) is chosen from alkali metal or alkaline earth metal (bi)carbonates, preferably alkali metal (bi)carbonates.

Mention may be made of sodium, potassium, magnesium and calcium carbonates or hydrogencarbonates and their mixtures, and in particular of sodium hydrogencarbonate. These hydrogencarbonates can originate from a natural water, for example spring water from the Vichy basin or from La Roche-Posay, or Badoit water (cf. patent, for example the document FR 2 814 943). Mention may in particular be made of sodium carbonate [497-19-8]=$Na_2CO_3$, sodium hydrogencarbonate or sodium bicarbonate [144-55-8]=$NaHCO_3$, and sodium dihydrogencarbonate=$Na(HCO_3)_2$.

An alternative form of the invention consists in using at least two compounds vi).

According to the invention, the basic compound(s) with a pKa greater than 7 used preferably represent(s) from 0.001% to 20% by weight of the total weight of the composition(s) containing the (bi)carbonate agent(s) and more preferably still from 0.005% to 10% by weight and better still from 0.1% to 5% by weight.

vii) Water

According to one embodiment of the invention, water is preferably included in the process of the invention. It can originate from the moistening of the keratinous substances, in particular of the keratinous fibres, and/or from the compositions A and/or B comprising the compounds i) to iv) as defined above or from one or more other compositions. Preferably, the water originates from at least one composition comprising at least one compound chosen from i) to iv) as defined above.

Preferably, the compositions A and B used in the process according to the invention each comprise water or a mixture of water and of one or more organic solvents or a mixture of organic solvents.

"Organic solvent" is understood to mean an organic substance which is capable of dissolving or dispersing another substance without chemically modifying it.

Mention may be made, as organic solvent, for example, of lower $C_1$-$C_4$ alkanols, such as ethanol and isopropanol; polyols and polyol ethers, such as 2-butoxyethanol, propylene glycol, propylene glycol monomethyl ether, diethylene glycol monoethyl ether, diethylene glycol monomethyl ether or hexylene glycol; and also aromatic alcohols, such as benzyl alcohol or phenoxyethanol.

The organic solvents are present in proportions preferably of between 1% and 40% by weight approximately and more preferably still between 5% and 30% by weight approximately, with respect to the total weight of the dyeing composition.

The Adjuvants

The compositions of the dyeing process in accordance with the invention can also include various adjuvants conventionally used in hair dyeing compositions, such as anionic, cationic, non-ionic, amphoteric or zwitterionic polymers or their mixtures, the said polymers being distinct from the thickening polymers defined above, inorganic thickening agents, antioxidants, penetrating agents, sequestering agents, fragrances, buffers, dispersing agents, conditioning agents, such as, for example, volatile or non-volatile and modified or unmodified silicones, fatty substances, film-forming agents, ceramides, preservatives or opacifying agents.

According to a specific embodiment, the composition A and/or the composition B, in particular the composition A, comprise less than 10% by weight, preferably less than 5% by weight and better still less than 2% by weight of fatty substance, preferably less than 10% by weight, preferably less than 5% by weight and better still less than 2% by weight of oil(s), with respect to the total weight of the composition A and/or B.

The above adjuvants are generally present in an amount of for each of them between 0.01% and 40% by weight, with respect to the weight of each composition comprising the ingredients i) to iv) as defined above, preferably between 0.1% and 20% by weight, with respect to the weight of the composition.

Of course, a person skilled in the art will take care to choose this or these optional additional compound or compounds so that the advantageous properties intrinsically attached to the composition or to the compositions of use in the dyeing process in accordance with the invention are not, or not substantially, detrimentally affected by the envisioned addition or additions.

The Additional Dyes

The process employing the ingredients i) to iv) as defined above can in addition employ or comprise one or more additional direct dyes. These direct dyes are chosen, for example, from those conventionally used in direct dyeing, and among which mention may be made of any commonly used aromatic and/or non-aromatic dye, such as neutral, acidic or cationic nitrobenzene direct dyes, neutral, acidic or cationic azo direct dyes, natural direct dyes other than ortho-diphenols, neutral, acidic or cationic quinone and in particular anthraquinone direct dyes, azine, triarylmethane, indoamine, methine, styryl, porphyrin, metalloporphyrin, phthalocyanine and methine cyanine direct dyes, and fluorescent dyes. All these additional dyes are other than the ortho-diphenol derivatives according to the invention.

Mention may be made, among natural direct dyes, of lawsone, juglone, indigo, isatin, curcumin, spinulosin, apigenidin and orceins. Use may also be made of extracts or decoctions containing these natural dyes and in particular henna-based extracts or poultices.

The additional direct dye(s) used in the composition(s) comprising the ingredients i) to iv) used in the process according to the invention preferably represent from 0.001% to 10% by weight approximately of the total weight of the composition(s) containing them and more preferably still from 0.05% to 5% by weight approximately.

The compositions of the process employing the ingredients i) to iv) as defined above can also employ one or more oxidation bases and/or one or more couplers conventionally used for dyeing keratinous fibres.

Mention may be made, among the oxidation bases, of para-phenylenediamines, bis(phenyl)alkylenediamines, para-aminophenols, bis-para-aminophenols, ortho-aminophenols, heterocyclic bases and their addition salts.

Mention may in particular be made, among these couplers, of meta-phenylenediamines, meta-aminophenols, meta-diphenols, naphthalene couplers, heterocyclic couplers and their addition salts.

The oxidation base(s) present in the composition(s) are generally each present in an amount of between 0.001% and 10% by weight of the total weight of the corresponding composition(s).

Acidifying or Basifying Agents

The pH of the compositions used in the process according to the invention can be adjusted to the desired value by means of acidifying or basifying agents generally used in the dyeing of keratinous fibres or alternatively with the help of conventional buffer systems.

Mention may be made, among the acidifying agents for the compositions used in the invention, by way of example, of inorganic or organic acids, such as hydrochloric acid, orthophosphoric acid, sulfuric acid, carboxylic acids, such as acetic acid, tartaric acid, citric acid or lactic acid, or sulfonic acids.

An advantageous alternative form is to add a basifying agent to the composition(s) of the dyeing process containing the (bi)carbonate(s). More particularly, this alkaline agent is chosen from aqueous ammonia, alkali metal carbonates, alkanolamines, such as monoethanolamine, diethanolamine or triethanolamine, and also their derivatives, sodium hydroxide, potassium hydroxide and the compounds of following formula (II):

(II)

in which W is a propylene residue optionally substituted with a hydroxyl group or a $C_1$-$C_4$ alkyl radical and $R_a$, $R_b$, $R_c$ and $R_d$, which are identical or different, represent a hydrogen atom or a $C_1$-$C_4$ alkyl or $C_1$-$C_4$ hydroxyalkyl radical.

Dyeing Process

The process according to the invention comprises:
   a) applying the composition A comprising the compounds i) to iii) to the keratinous substances,
   b) optionally wiping mechanically and/or drying and/or rinsing the said keratinous substances,
   c) applying the composition B comprising the compound iv), optionally in the presence of hydrogen peroxide or of one or more system(s) which generate(s) hydrogen peroxide and of one or more (bi)carbonate(s).

The compositions A and B are applied to the keratinous substances sequentially, whatever their order of application (application of the composition A and then of the composition B or application of the composition B and then of the composition A).

According to one embodiment, the composition A is applied and then the composition B, with an optional intermediate step of b) wiping mechanically and/or drying and/or rinsing the said keratinous substances, The keratinous substances, in particular the keratinous fibres, may or may not be moistened beforehand.

The application of the compositions A and B can be preceded or followed by a stage of rinsing and/or drying the keratinous substances.

According to one embodiment, the process according to the invention comprises at least one stage of rinsing (final or intermediate).

According to one embodiment, the process according to the invention does not comprise a final rinsing stage.

According to a preferred process of the invention, the keratinous substances are rinsed before application of the composition B.

The period of time between the stages of application of the compositions A and B can be between 5 seconds and 120 minutes, preferably between 20 seconds and 60 minutes and more particularly between 30 seconds and 30 minutes.

According to one embodiment, after the final stage of treatment with the compounds i) to iv), the said fibres are not rinsed.

The drying stage, if it takes place, can be carried out via a thermal drying means, for example a hair dryer, hairstyling hood or smoothing iron or in the open air, and then the fibres are dried until the wet appearance of the hair has disappeared visually. In particular, the keratinous fibres are dried using a smoothing iron or a hair dryer.

The process for dyeing the keratinous fibres according to the invention can comprise at least one intermediate stage of mechanical wiping of the fibres.

Mechanical wiping of the fibres is understood to mean the rubbing of an absorbent article over the fibres and the physical removal by the absorbent article of the excess ingredient(s) which have not penetrated into the fibres. The absorbent article can be a piece of fabric, such as a towel, particularly a terry cloth, a dish towel or absorbent paper, such as a household roll towel.

According to a particularly advantageous process of the invention, the mechanical wiping is performed without total drying of the fibre, leaving the fibre moist.

Whatever the mode of application, the temperature for application of the ingredients i) to iv) is generally between ambient temperature (15° C. to 25° C.) and 80° C. and more particularly between 15° C. and 45° C. Thus, after application of the composition according to the invention, the head of hair can advantageously be subjected to a heat treatment by heating to a temperature of between 30° C. and 60° C.

When, in the process, it is used a thermal heating means such as a heating iron its temperature of between 60 and 220° C. and preferably between 120 and 200° C.

A specific embodiment of the invention relates to a dyeing process which is carried out at ambient temperature (25° C.) for the application of the ingredients i) to iv).

The following example serves to illustrate the invention without, however, exhibiting a limiting nature.

I) DYEING EXAMPLES

The following compositions were prepared (amounts expressed in g % of starting material in unmodified form):

|  | A1 | A2 | A3 (Invention) |
|---|---|---|---|
| Hydroxyethylcellulose | 1 | 1 | 1 |
| ($C_8/C_{16}$) ALKYL1,4-POLYGLUCOSIDE AS A 53% AQUEOUS SOLUTION (PLANTACARE 818 UP FROM COGNIS) | 7 |  | 7 |
| Sodium lauryl ether sulfate (70% as AM in water) |  | 7 |  |
| Manganese gluconate | 0 | 0.05 | 0.05 |
| Water | q.s. 100 | q.s. 100 | q.s. 100 |

|  | B |
|---|---|
| 50% by volume aqueous hydrogen peroxide solution | 1.2 |
| Sodium bicarbonate | 2.5 |
| Extract of pine (*Pinus pinaster*) bark (Fixopin from DRT) | 2.5 |
| Ethanol | 10 |

Each composition A1, A2 and A3 is applied to locks of natural hair containing 90% white hairs moistened beforehand, with a bath ratio of 0.5 g of formulation per 1 g of hair. The composition is subsequently allowed to act for 1 minute at ambient temperature and the locks are rinsed with water with 6 passes between the fingers.

The hair is subsequently superficially dried using an absorbent towel in order to remove the excess formulation.

The composition B is subsequently applied to the hair with a bath ratio of 0.5 g per 1 g of lock; no rinsing is carried out.

After a few minutes, a very intense colouration appears.

Colorimetric Results:

The colouration of the hair is evaluated with a Minolta spectrocolorimeter (CM3600d, illuminant D65, angle 10°, SCI values) in the CIE Lab system.

In this L*a*b* system, L* represents the intensity of the colour, a* indicates the green/red colour axis and b* indicates the blue/yellow colour axis. The lower the value of L*, the darker or more intense the colour. The higher the value of a*, the redder the shade and, the higher the value of b*, the yellower the shade.

The variation in colouration of the locks before treatment (control) and after treatment is represented by (ΔE*) according to the following equation:

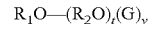

$$\Delta E^* = \sqrt{(L^*-L_o^*)^2 + (a^*-a_o^*)^2 + (b^*-b_o^*)^2}$$

In this equation, L*, a* and b* represent the values measured after dyeing natural hair comprising 90% white hairs and $L^*_0$, $a_0^*$ and $b_0^*$ represent the values measured for untreated natural hair comprising 90% white hairs.

The higher the value of ΔE*, the greater the difference in colour between the control locks and the dyed locks.

The following results are obtained:

|  | Natural white hairs | After application of B alone | After application of A1 and B | After application of A2 and B | After application of A3 and B |
|---|---|---|---|---|---|
| L* | 63.6 | 58.3 | 59.1 | 56.5 | 51.1 |
| a* | 0.6 | 3.4 | 4.5 | 8.9 | 9.2 |
| b* | 13.4 | 14.9 | 16.4 | 20.2 | 20.1 |
| ΔE* |  | 6.2 | 6.7 | 12.9 | 16.6 |

It emerges from the above results that the process according to the invention employing a composition A as defined according to the invention makes possible a much better colouration of the hair than the comparative processes.

The invention claimed is:

1. A process for treatment of keratinous substances, comprising:
   applying to the keratinous substances a first composition that comprises:
   at least one non-ionic alkylpolyglucoside surfactant;
   at least one metal salt; and
   at least one thickening polymer;
   optionally wiping mechanically, drying, or rinsing the keratinous substances; and
   applying to the keratinous substances a second composition, wherein the second composition comprises at least one ortho-diphenol derivative.

2. The process of claim 1, wherein the at least one non-ionic alkylpolyglucoside surfactant is chosen from compounds of the formula below:

$$R_1O-(R_2O)_t(G)_v$$

wherein:
   $R_1$ represents a linear or branched alkyl, or alkenyl radical, comprising from 8 to 24 carbon atoms, or an alkylphenyl radical of which a linear or branched alkyl radical comprises from 8 to 24 carbon atoms;
   $R_2$ represents an alkylene radical comprising from 2 to 4 carbon atoms;
   G represents a sugar unit comprising from 5 to 6 carbon atoms;
   t is a number ranging from 0 to 10; and
   v is a number ranging from 1 to 15.

3. The process of claim 2, wherein:
R₁ represents a saturated or unsaturated, linear or branched alkyl radical comprising from 8 to 18 carbon atoms;
t is a number ranging from 0 to 3;
G represents glucose, fructose or galactose; and
v is a number ranging from 1 to 15.

4. The process of claim 1, wherein the at least one non-ionic alkylpolyglucoside surfactant is present in the first composition in an amount ranging from about 0.1% to about 30% by weight of active material relative to the total weight of the first composition.

5. The process of claim 1, wherein the at least one metal salt is chosen from Mn salts or Zn salts.

6. The process of claim 5, wherein the Mn salts and Zn salts are independently chosen from halides, sulfates, phosphates, nitrates, perchlorates, carboxylic acid salts, or mixtures thereof.

7. The process of claim 1, wherein the at least one metal salt is present in the first composition in an amount ranging from about 0.001% to about 10% by weight of active material relative to the total weight of the first composition.

8. The process of claim 1, wherein the at least one thickening polymer is chosen from polymers having at least one sugar unit.

9. The process of claim 1, wherein the at least one thickening polymer is chosen from tree or shrub exudates, gums resulting from algae, gums resulting from seeds or tubers, microbial gums, or plant extracts.

10. The process of claim 1, wherein the at least one thickening polymer is chosen from celluloses or their derivatives.

11. The process of claim 1, wherein the at least one thickening polymer is present in the first composition in an amount ranging from about 0.01% to about 10% by weight of active material relative to the total weight of the first composition.

12. The process of claim 1, wherein the at least one ortho-diphenol derivative is chosen from natural ortho-diphenol derivatives.

13. The process of claim 12, wherein the natural ortho-diphenols are chosen from extracts of animals, bacteria, fungi, algae, or plants.

14. The process of claim 1, wherein the at least one ortho-diphenol derivative comprises an ortho-diphenol having an aromatic ring chosen from benzene, naphthalene, tetrahydronaphthalene, indane, indene, anthracene, phenanthrene, isoindole, indoline, isoindoline, benzofuran, dihydrobenzofuran, chroman, isochroman, chromene, isochromene, quinoline, tetrahydroquinoline, or isoquinoline, wherein the aromatic ring has at least two hydroxyl groups carried by two adjacent contiguous carbon atoms of the aromatic ring.

15. The process of claim 1, wherein the at least one ortho-diphenol derivative is chosen from compounds of formula (I) below or one of its oligomers, in salified or non-salified form:

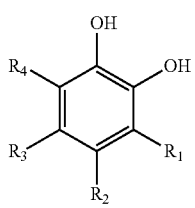

(I)

wherein:

$R_1$ to $R_4$ each independently represent a hydrogen atom, a halogen atom, a hydroxyl radical, a carboxyl radical, an alkyl carboxylate or alkoxycarbonyl radical, an optionally substituted amino radical, an optionally substituted and linear or branched alkyl radical, an optionally substituted and linear or branched alkenyl radical, an optionally substituted cycloalkyl radical, an alkoxy radical, an alkoxyalkyl radical, an alkoxyaryl radical having an optionally substituted aryl group, an aryl radical, a substituted aryl radical, a saturated or unsaturated heterocyclic radical optionally carrying a cationic or anionic charge and optionally substituted or fused with a substituted or unsubstituted aromatic ring, or a radical containing one or more silicon atoms; and two of the substituents carried by two adjacent carbon atoms $R_1$—$R_2$, $R_2$—$R_3$ or $R_3$—$R_4$ together form a saturated or unsaturated, aromatic or non-aromatic, and substituted or unsubstituted ring.

16. The process of claim 1, wherein the at least one ortho-diphenol derivative is chosen from:

flavonols, anthocyanidins, anthocyanins or anthocyans, ortho-hydroxybenzoates, flavones, hydroxystilbenes, 3,4-dihydroxyphenylalanine and its derivatives, 2,3-dihydroxyphenylalanine and its derivatives, 4,5-dihydroxyphenylalanine and its derivatives, dihydroxycinnamates, ortho-polyhydroxycoumarins, ortho-polyhydroxyisocoumarins, ortho-polyhydroxycoumarones, ortho-polyhydroxyisocoumarones, ortho-polyhydroxychalcones, ortho-polyhydroxychromones, polyhydroxyquinones, orthohydroxyxanthones, 1,2-dihydroxybenzene and its derivatives, 1,2,4-trihydroxybenzene and its derivatives, 1,2,3-trihydroxybenzene and its derivatives, 2,4,5-trihydroxytoluene and its derivatives, proanthocyanidins, proanthocyanins, tannic acid, ellagic acid, or mixtures thereof.

17. The process of claim 1, wherein:

the first composition and/or the second composition further comprises at least one fatty substance in an amount less than about 10% by weight relative to the total weight of the first composition and/or the second composition; and the first composition and/or the second composition further comprises at least one oil in an amount less than about 10% by weight relative to the total weight of the first composition and/or the second composition.

18. The process of claim 1, wherein the first composition further comprises at least one anionic surfactant in an amount less than about 1% by weight relative to the total weight of the first composition.

19. The process of claim 1, wherein the first composition is applied to the keratinous substances prior to application of the second composition to the keratinous substances.

20. The process of claim 1, wherein the keratinous substances are not rinsed following application of the first composition and the second composition.

* * * * *